(12) United States Patent
Metzinger et al.

(10) Patent No.: US 8,961,522 B2
(45) Date of Patent: Feb. 24, 2015

(54) FLEXIBLE SHAFT REDUCTION TOOL

(75) Inventors: Anthony J. Metzinger, Winona Lake, IN (US); David A. Hawkes, Layton, UT (US)

(73) Assignee: Biomet C.V., Gibraltar (GI)

(*) Notice: Subject to any disclaimer, the term of this patent is extended or adjusted under 35 U.S.C. 154(b) by 1558 days.

(21) Appl. No.: 11/657,830

(22) Filed: Jan. 25, 2007

(65) Prior Publication Data

US 2008/0183170 A1 Jul. 31, 2008

(51) Int. Cl.
| | | |
|---|---|---|
| A61B 17/70 | (2006.01) | |
| A61B 17/72 | (2006.01) | |
| A61B 17/88 | (2006.01) | |
| A61B 17/92 | (2006.01) | |
| A61B 17/00 | (2006.01) | |

(52) U.S. Cl.
CPC ......... *A61B 17/7208* (2013.01); *A61B 17/8897* (2013.01); *A61B 17/921* (2013.01); *A61B 2017/0046* (2013.01)
USPC .......................................... 606/86 R; 606/62

(58) Field of Classification Search
USPC ................ 606/62–68, 86 R, 87, 96, 105
See application file for complete search history.

(56) References Cited

U.S. PATENT DOCUMENTS

| 3,439,671 | A | | 4/1969 | Küntscher | |
| 4,800,873 | A | * | 1/1989 | Audell | 606/62 |
| 5,122,146 | A | | 6/1992 | Chapman et al. | |
| 5,135,527 | A | | 8/1992 | Ender | |
| 5,174,302 | A | | 12/1992 | Palmer | |
| 5,387,218 | A | * | 2/1995 | Meswania | 606/96 |
| 5,488,761 | A | * | 2/1996 | Leone | 29/2.25 |
| 5,509,919 | A | | 4/1996 | Young | |
| 5,624,447 | A | | 4/1997 | Myers | |
| 5,879,352 | A | * | 3/1999 | Filoso et al. | 606/62 |
| 5,951,561 | A | | 9/1999 | Pepper et al. | |
| 6,053,922 | A | * | 4/2000 | Krause et al. | 606/80 |
| 6,074,392 | A | | 6/2000 | Durham | |
| 6,783,530 | B1 | * | 8/2004 | Levy | 606/63 |
| 2002/0165544 | A1 | * | 11/2002 | Perren et al. | 606/63 |
| 2003/0181918 | A1 | * | 9/2003 | Smothers et al. | 606/86 |
| 2004/0162559 | A1 | * | 8/2004 | Arramon et al. | 606/62 |
| 2005/0192579 | A1 | | 9/2005 | Jackson | |

FOREIGN PATENT DOCUMENTS

| CA | 2 535 454 | 2/2005 |
| EP | 1018318 | 7/2000 |
| WO | WO03068090 | 8/2003 |

* cited by examiner

*Primary Examiner* — Eduardo C Robert
*Assistant Examiner* — Steven Cotroneo
(74) *Attorney, Agent, or Firm* — Harness, Dickey

(57) ABSTRACT

A bone reduction method and apparatus includes a bone reduction tool including a shaft with a proximal end portion, a distal end portion for insertion into a fractured bone, a first rigid portion located at the distal end portion, and a first flexible portion located between the first rigid portion and the proximal end portion.

5 Claims, 5 Drawing Sheets

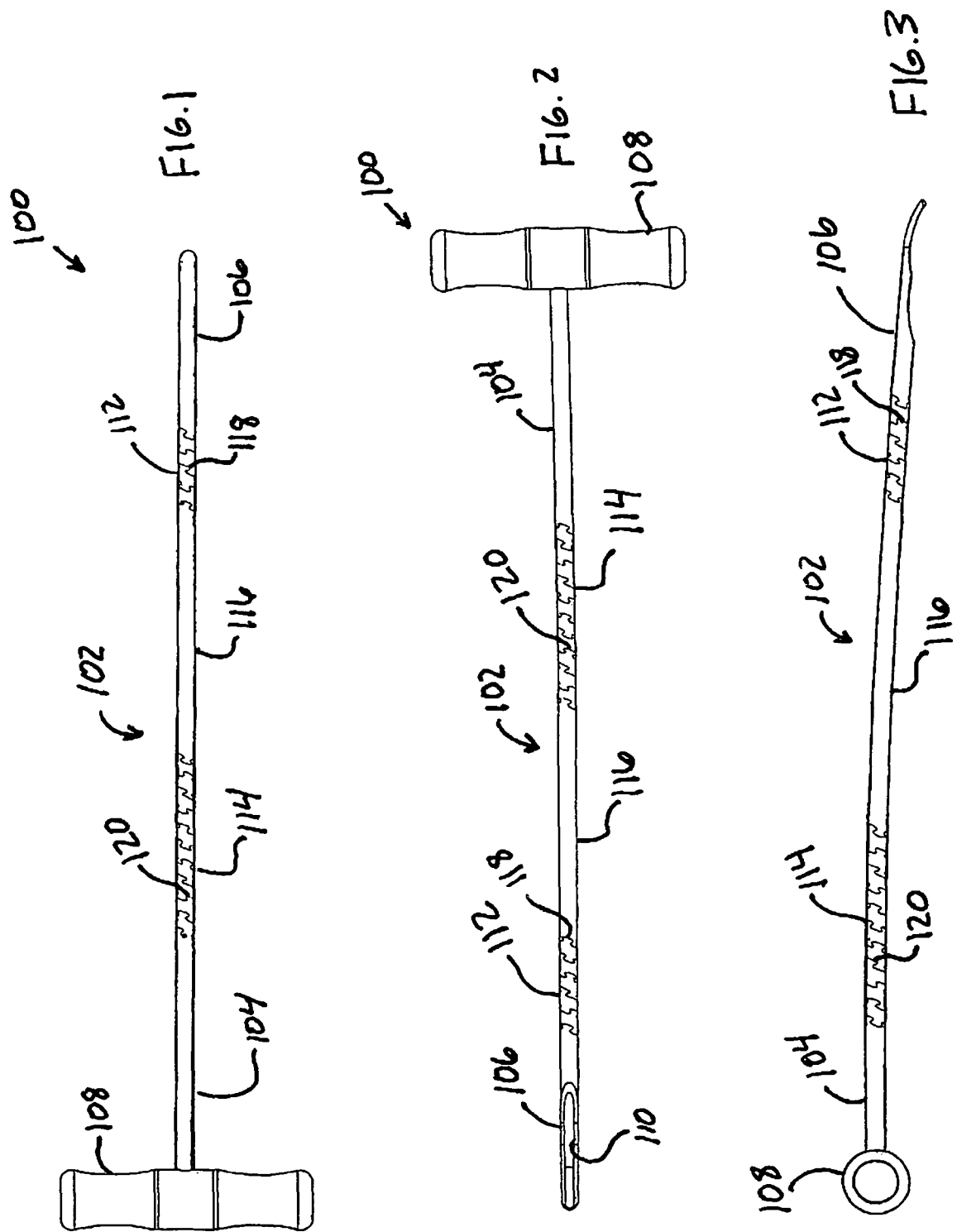

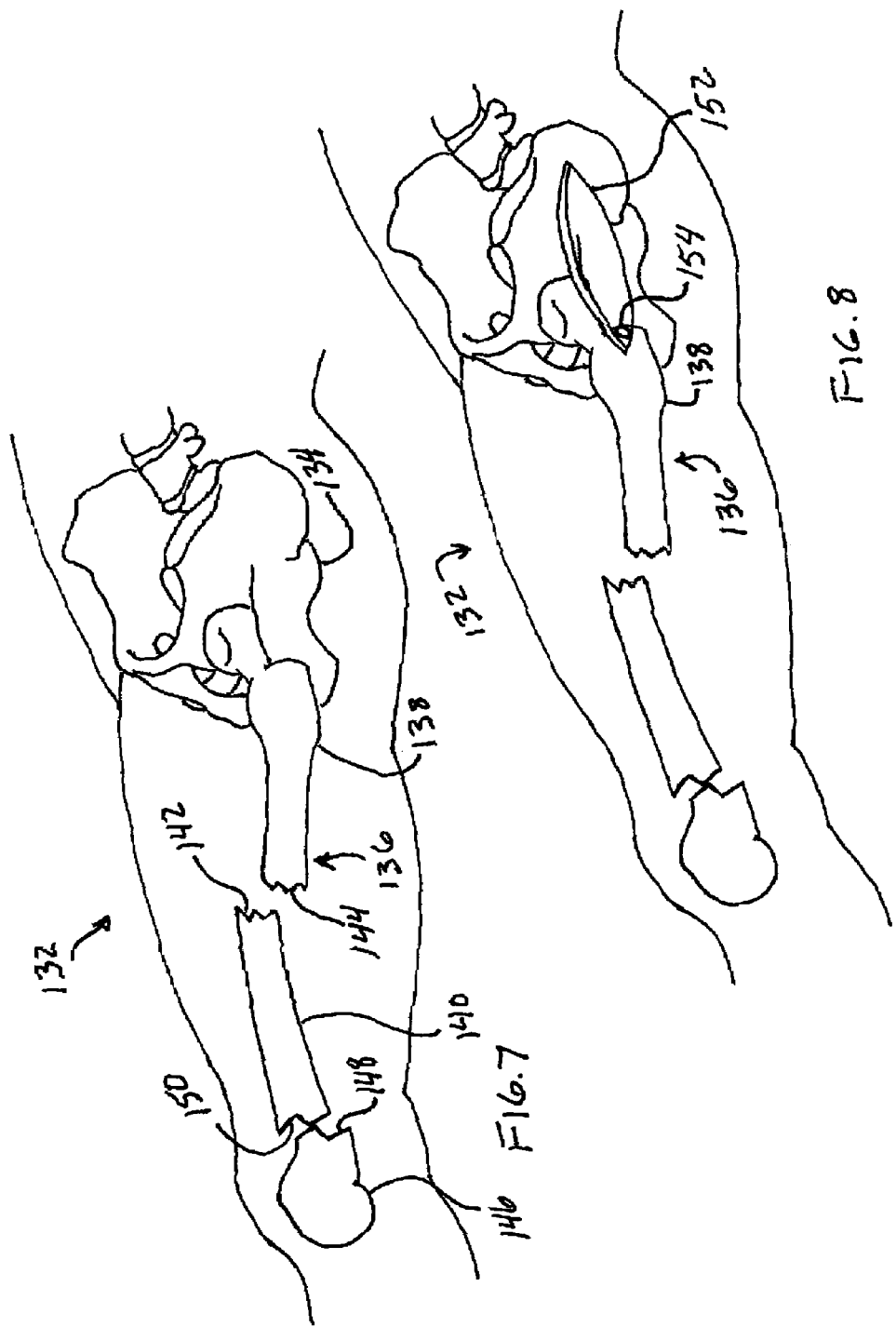

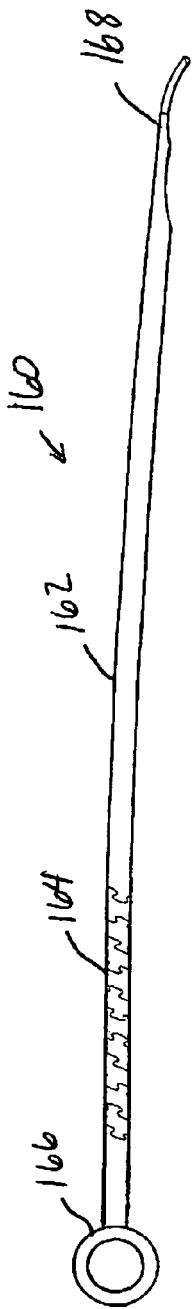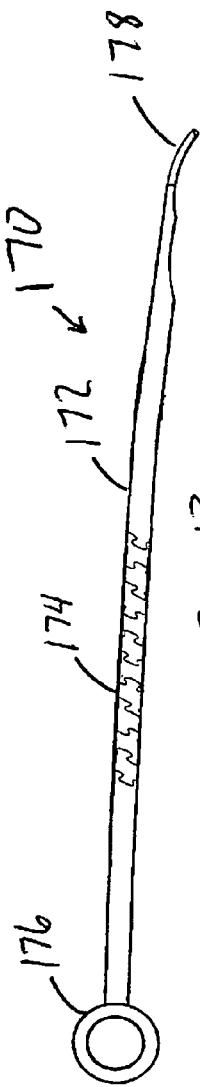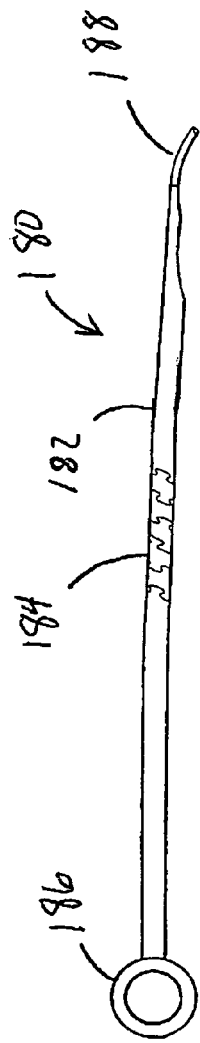

FLEXIBLE SHAFT REDUCTION TOOL

FIELD OF THE INVENTION

This invention relates to the field of orthopaedics and more particularly to methods and tools for setting fractures.

BACKGROUND

Fractures of long bones such as the femur are fairly common. Various techniques are employed for holding together parts of a fractured bone during the healing process. Prior to the fixation of the bone fragments, however, it is first required that the fracture be reduced, that is, the various bone fragments or pieces must be repositioned in their proper relative arrangement before the fractured bone can be fixed or stabilized for healing. A great many devices have been proposed for the reduction of fractures of this type. While many of these devices have found application and have advantages relative one to another, there remain some problems and areas of continuing concern.

In one device, fixation pins are inserted through the bone fragments to provide for the desired reduction. Although this device is said to be able to reduce the fracture, it involves a relatively complicated procedure in that movement of one component will affect the orientation of any other component. Furthermore, rotation is limited in view of the skin and tissue through which the pins penetrate.

Elastic nails have also been used to provide reduction. The nails are passed into the intramedullary canal of a bone through a hole in the bone and are then rotated so as to reduce the fractured femoral head using the entry point into the intramedullary canal as a fulcrum. Since the bone hole serves as a fulcrum point, elastic nails are not generally capable of fine adjustment or ease of use within the intramedullary canal. Moreover, because the entire length of the nails is elastic, fine control over the positioning of the distal end of the nail is difficult.

What is needed, therefore, is a reduction tool and method which provides improved reduction capabilities. What is further needed is a tool and method which reduces damage to soft tissue while allowing reduction of bone fragments which are misaligned.

SUMMARY

A bone reduction assembly and method is disclosed. In one embodiment, a bone reduction tool includes a shaft with a proximal end portion, a distal end portion for insertion into a fractured bone, a first rigid portion located at the distal end portion, and a first flexible portion located between the first rigid portion and the proximal end portion.

In one embodiment, a method of reducing a fractured bone includes exposing a first portion of a fractured bone having a first intramedullary canal portion, inserting a rigid distal portion of a reduction device into the first intramedullary canal portion, inserting a first flexible portion of the reduction device into the first intramedullary canal portion after inserting the rigid distal portion into the first intramedullary canal portion, and manipulating the reduction device to reduce the fractured bone.

In a further embodiment, a bone reduction tool includes a shaft with a rigid distal end portion, a rigid proximal end portion, and at least one flexible portion located between the rigid distal end portion and the rigid proximal end portion, and a handle operatively connected to the rigid proximal end portion.

BRIEF DESCRIPTION OF THE DRAWINGS

FIG. 1 depicts top plan view of a bone reduction tool incorporating three rigid shaft portions and two flexible shaft portions in accordance with principles of the present invention;

FIG. 2 depicts a bottom plan view of the bone plate of the bone reduction tool of FIG. 1;

FIG. 3 depicts a side plan view showing the hook shape of the distal end of the bone plate of the bone reduction tool of FIG. 1;

FIG. 7 depicts a schematic diagram of a thigh area wherein a femoral bone is fractured into three bone fragments, none of the bone fragments aligned with the other bone fragments, and the leg is in traction in accordance with principles of the present invention;

FIG. 8 depicts the thigh area of FIG. 7 with an incision allowing access to the proximal femoral bone fragment and a bore made into the proximal femoral bone fragment exposing the intramedullary canal of the proximal femoral bone fragment;

FIGS. 12-14 depict side plan views of three different bone reduction tools with different shaft lengths, different placement of flexible shaft areas, and different flexibility of the flexible shaft areas that may be included in a kit in accordance with principles of the present invention.

DETAILED DESCRIPTION

Figure 4:
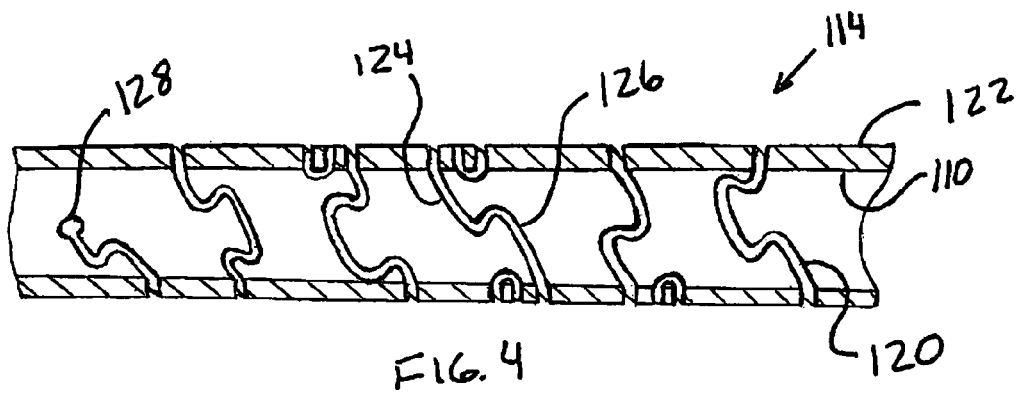
FIG. 4 depicts a partial cross-sectional view of a flexible portion of the bone reduction tool of FIG. 1.

FIG. 1 shows a bone reduction tool 100. The tool 100 includes an elongated, generally cylindrical shaft 102 with a proximal end portion 104 and a distal end portion 106. A T-shaped handle 108 is attached to the proximal end portion 104. The shaft 102 has an internal bore 110 extending completely along the longitudinal axis of the tool 100 from the T-shaped handle 108 to the distal end portion 106 which can be seen in FIG. 2. The distal end portion 106 is hook shaped when viewed from the side as best seen in FIG. 3.

Two flexible shaft portions 112 and 114 separate a medial shaft portion 116 from the distal end portion 106 and the proximal end portion 104, respectively. The flexible shaft portions 112 and 114 in this embodiment include slits 118 and 120. The slits 118 and 120 extend in a generally helical fashion along the longitudinal axis of the tool 100. Details of the slits 118 and 120, which in this embodiment are similar, are explained with reference to FIG. 4. The slit 120 extends from the outer surface 122 of the shaft 102 to the bore 110. The slit 120 is in the form of a continuous chain of alternating partial links such as partial links 124 and 126. Each end of the slit 120 includes a bore such as bore 128. The bore 128 alleviates stress at the end of the slit 120 as the tool flexes as discussed below.

The main difference between the slit 120 and the slit 118, in addition to the relative location of the slits 118 and 120 along the shaft 102, is the length of the slits 118 and 120. As shown in FIGS. 1-3, the slit 120 extends along the shaft 102 for a greater distance than the slit 118. In this embodiment, the flexible shaft portion 112 extends about 5 centimeters along the shaft 102 while the flexible shaft portion 114 extends about 10 centimeters along the shaft 102. The result is that the flexible shaft portion 114 is more flexible than the flexible shaft portion 112.

Specifically, the entire shaft 102 in this embodiment is made from a resilient material. Accordingly, the slits 118 and 120 effectively weaken the structure of the shaft 102. Consequently, while the alternating partial link structure provides sufficient strength and rigidity for the shaft 102, the slits 118 and 120 allow the flexible shaft portions 112 and 114, respectively, to be more flexible than the more rigid proximal end portion 104, distal end portion 106 and medial shaft portion 116. Since the slit 120 extends along the shaft 102 for a greater distance than the slit 118, the flexible shaft portion 114 is more weakened than the flexible shaft portion 112, and thus more easily flexed. The same result may be effected by modifying the relative width of the slits or the pitch of the slits since a given area will become more flexible as the amount of material within the area is decreased.

Figure 5:
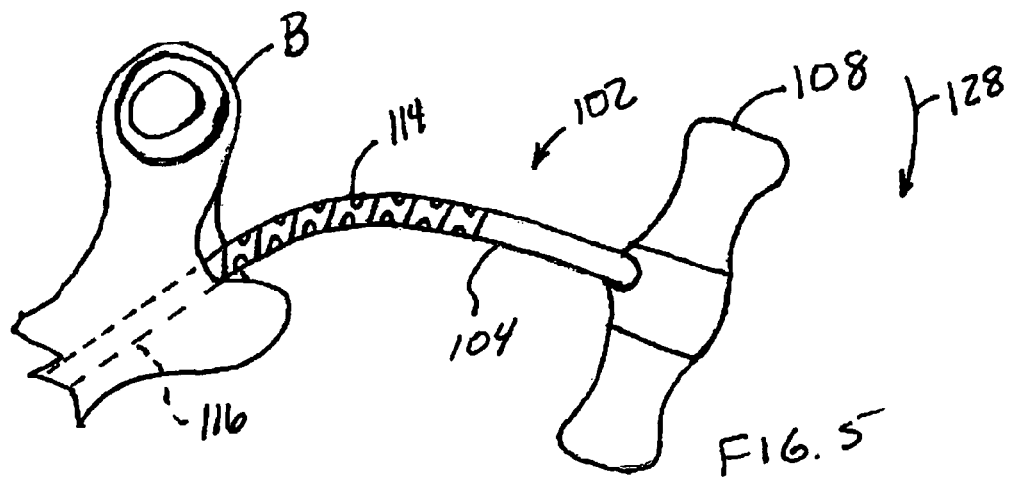
FIG. 5 depicts the flexible portion of FIG. 4 flexed to about 45 degrees while the adjacent rigid portions of the shaft remain unflexed.
Figure 6:
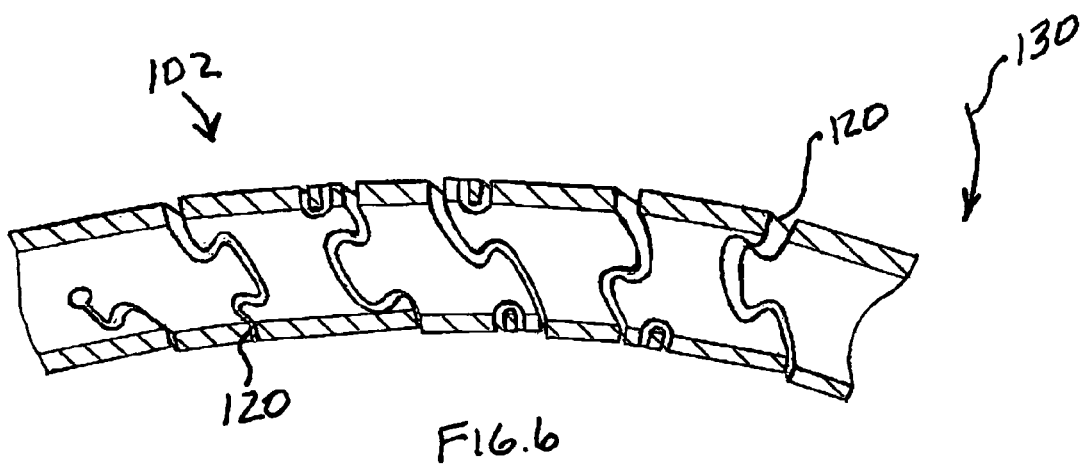
FIG. 6 depicts a partial cross-sectional view of the flexible shaft portion of FIG. 5 showing a widening of the slit in the flexible shaft portion at the top of the flexible shaft portion as viewed in FIG. 6 and a narrowing of the slit in the flexible shaft portion at the bottom of the flexible shaft portion.

Thus, as shown in FIG. 5, when force is applied to the handle 108 in the direction of the arrow 128 while movement of the distal end portion 106 of the shaft 102 is restricted, such as by a bone B, the flexible shaft portion 114 bends while the more rigid proximal end portion 104 and medial shaft portion 116 remain straight. Thus, as shown in FIG. 6, the width of the slit 120 at the side of the shaft 102 from which the force is applied, as indicated by the arrow 130, increases while the width of the slit 120 at the opposite side of the shaft 102 decreases. Once the flexible shaft portion 114 has been bent so that the sides of the slit 120 abut each other, most of any additional force applied in an attempt to further bend the shaft 102 will be passed through the flexible shaft portion 114. Thus, the width of the slit 120, along with the orientation and pattern of the slit 120, can be modified to allow for greater or lesser extents of flex.

The relative locations of the flexible shaft portions 112 and 114, along with the relative flexibility of the flexible shaft portions 112 and 114, are selected to provide the desired amount of fine control at the distal end portion 106 while allowing the handle 108 to be positioned to allow entry of the tool 100 into a bone while minimizing the impingement of the tool 102 on soft tissues proximate to the bone. This is further described with reference to FIGS. 7-11 which describe one method of reducing a fracture.

Referring to FIG. 7, a partial schematic representation of the thigh area 132 of a patient is shown including a hip bone 134 and thigh (femur) bone 136. The femur 136 is fractured into a proximal bone fragment 138 and a medial bone fragment 140 at the fractured ends 142 and 144. The femur 136 is further fractured into a distal bone fragment 146 at the fractured ends 148 and 150. Initially, the thigh 132 is placed into traction in accordance with an appropriate procedure. This causes the fractured end 142 of the medial bone fragment 140 to be positioned leftwardly of the fractured end 144 of the proximal bone fragment 138 as viewed in FIG. 7. Likewise, the fractured end 148 of the distal bone fragment 146 is positioned leftwardly of the fractured end 150 of the medial bone fragment 140.

Next, the surgical site is prepared in accordance with acceptable practices and an incision 152 is made in the thigh 132 to expose the femur 136 as shown in FIG. 8. A hole 154 is made in the exposed surface of the proximal bone fragment 138 such as by use of an awl (not shown) to expose the intramedullary canal of the proximal bone fragment 138. The intramedullary canal of the proximal bone fragment 138 is then reamed.

Figure 9:
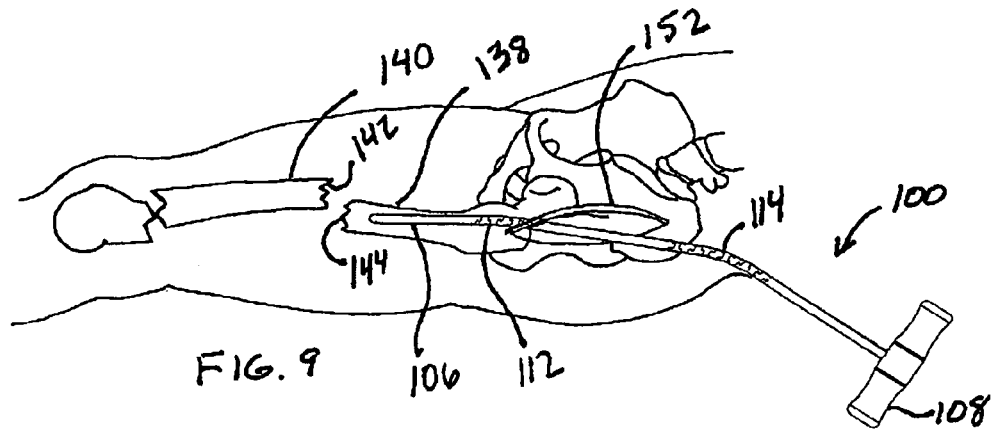
FIG. 9 depicts the thigh area of FIG. 8 with the distal end portion and one flexible shaft portion of the reduction tool of FIG. 1 inserted within the intramedullary canal of the proximal femoral bone fragment.

Once the intramedullary canal of the proximal bone fragment 138 is reamed, the distal end portion 106 of the tool 100 is inserted through the incision 152 and the hole 154 into the intramedullary canal of the proximal bone fragment 138. As the tool 100 is inserted, the flexible shaft portion 112 may be flexed as necessary to allow the distal end portion 106 to be moved past minor obstacles as shown in FIG. 9.

Figure 10:
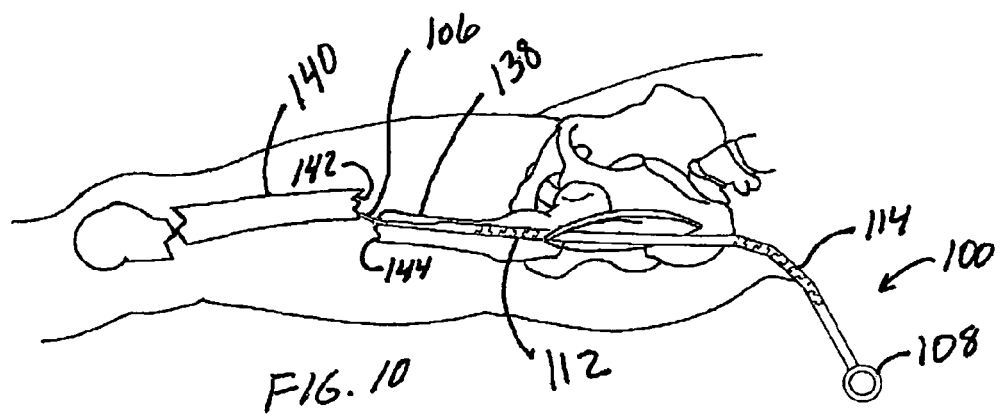
FIG. 10 depicts the thigh area of FIG. 8 after the reduction tool has been rotated with the second flexible shaft area bent and the distal end portion of the reduction tool hooked into the intramedullary canal of the offset medial bone fragment portion.

As the distal end portion 106 approaches the fractured end 142 of the medial bone fragment 140, the tool 100 may be rotated as necessary to "snag" the medial bone fragment 140 as shown in FIG. 10. The hooked shape of the distal end portion 106 provides, in conjunction with the flexible shaft portion 112, allows the distal end portion 106 to be inserted into the intramedullary canal of the medial bone fragment 140 even when significant offset exists between the fractured end 142 and the fractured end 144. Radiography may be used during this step to assist in positioning the tool 100.

The tool 100 is then manipulated, such as by rotation of the handle 108, to align the fractured end 142 and the fractured end 144. Radiography may also be used to assist in achieving the desired alignment. The location of the flexible shaft portion 114 allows the handle 108 to be freely moved without causing damage to the soft tissue surrounding the incision 152 or the femur 136.

Once the fractured end 142 and the fractured end 144 are aligned, the traction on the thigh 132 is eased, allowing the fractured end 142 and the fractured end 144 to abut one another. Next, a semi-flexible wire (not shown) (typically 3 millimeters in diameter) is inserted through the bore 110 in the handle 108 and the shaft 102. The semi-flexible wire or guidewire is inserted through the shaft 102 and across the fractured end 142 and the fractured end 144 into the medial bone fragment 140. Once the guidewire is positioned the tool 100 is removed and the medial bone fragment 140 is reamed.

Figure 11:
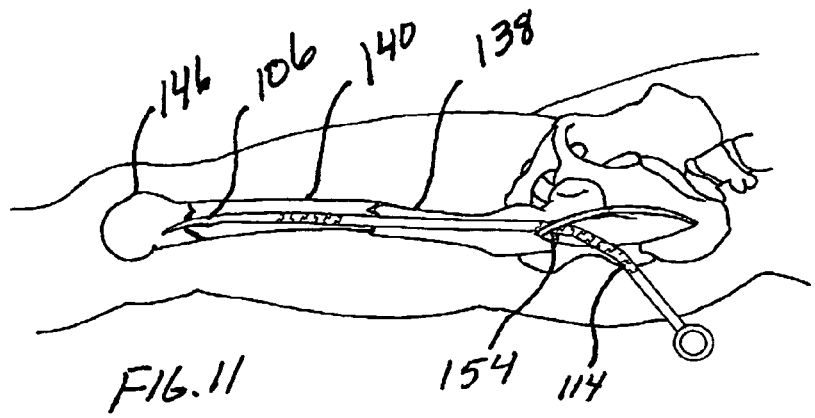
FIG. 11 depicts the thigh area of FIG. 8 with the three femoral bone fragments aligned and reduced with the shaft reduction tool inserted within the aligned intramedullary canal of the femoral bone while a flexible portion of the reduction tool is used to allow the handle of the reduction tool to be moved away from the thigh area.

The procedure set forth above for alignment of the fractured ends 142 and 144 is then repeated to align the fractured ends 148 and 150. Once the traction is released in this example, the femur 136 is aligned as shown in FIG. 11. The length of the tool 100 allows the distal end portion 016 to extend within the intramedullary canal from the hole 154 into the distal bone portion 146. When the tool 100 is fully inserted within the femur 136, the flexible shaft portion 114 is located proximate the hole 154 and extends outwardly of the incision 152. This allows the handle 108 to be freely maneuvered without causing undue disturbance of the soft tissues surrounding the incision 152 and the hole 154. The femur 136 may then be stabilized in accordance with the desired method, the tool 100 may be removed and the incision 152 may be closed.

In one embodiment, a second reduction tool may be used during a procedure. Thus, a kit may include a number of reduction devices, each of the reduction devices having different dimensions and different proportions so as to optimize the ability to reduce different fractures. Accordingly, while in this embodiment the distal end portion 106 is about 9 centimeters, the medial shaft portion is about 12.5 centimeters and the proximal end portion is about 5.5 centimeters, these proportions may be altered for various embodiments. Additionally, more or fewer flexible shaft portions may be provided in a particular tool.

By way of example, FIG. 12 depicts a bone reduction tool 160 which includes a shaft 162 with a flexible shaft portion 164 located between a handle 166 and a distal end portion 168. The flexible shaft portion 164 is located closer to the handle 166 than the distal end portion 168. Thus, the bone reduction tool 160 may be used when the fractured portions of a bone are relatively close in alignment but when access to the intramedullary area of the bone is constrained by soft tissue.

In a further embodiment, FIG. 13 depicts a bone reduction tool 170 which includes a shaft 172 with a flexible shaft portion 174 located between a handle 176 and a distal end portion 178. The flexible shaft portion 174 is located at about the center of the shaft 176. Additionally, the shaft 172 is shorter than the shaft 162. Thus, the bone reduction tool 170 may be used when the fractured portions of a bone are relatively close in alignment and when the fractured areas are closer to the entry point to the intramedullary area of the fractured bone.

In yet another embodiment, FIG. 14 depicts a bone reduction tool 180 which includes a shaft 182 with a flexible shaft portion 184 located between a handle 186 and a distal end portion 188. The flexible shaft portion 184 is located closer to the distal end portion 188 than the handle 186. Additionally, the shaft 182 is shorter than either the shaft 162 or the shaft 172. Another difference is that the flexible shaft portion 184 is shorter than the flexible shaft portion 164 or the flexible shaft portion 174. Thus, the bone reduction tool 180 may be used when access to the intramedullary area of a bone is less constrained by soft tissue and the fractured portions of a bone are not close in alignment. In a further embodiment, the radius of the bone reduction tools in a kit are varied to allow the use of bone reduction tools with smaller radiuses to be used in thinner intramedullary areas.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

We claim:

1. A bone reduction tool comprising:
a shaft including
a proximal end portion,
a distal end portion for insertion into a fractured bone,
a first rigid portion permanently located at a fixed location of the distal end portion, and
a first flexible portion located between the first rigid portion and the proximal end portion;
a guide wire bore extending through said shaft along the entire length thereof for receiving a guide wire therethrough, the shaft further comprising:
a second rigid portion located between the first flexible portion and the proximal end portion;
a second flexible portion located between the second rigid portion and the proximal end portion; and
a third rigid portion located at the proximal end portion, wherein the distal end portion is curved along a longitudinal axis of the shaft.

2. A bone reduction tool comprising:
a shaft including
a proximal end portion,
a distal end portion for insertion into a fractured bone,
a first rigid portion permanently located at a fixed location of the distal end portion, and
a first flexible portion located between the first rigid portion and the proximal end portion;
a guide wire bore extending through said shaft along the entire length thereof for receiving a guide wire therethrough, the shaft further comprising:
a second rigid portion located between the first flexible portion and the proximal end portion;
a second flexible portion located between the second rigid portion and the proximal end portion; and
a third rigid portion located at the proximal end portion,
wherein the first flexible portion comprises a first slit helically extending about a longitudinal axis of the first flexible portion through the shaft to the guide wire bore;
the second flexible portion comprises a second slit helically extending about a longitudinal axis of the second flexible portion; and
the second slit extends along the longitudinal axis of the second flexible portion for a distance greater than the distance which the first slit extends along the longitudinal axis of the first flexible portion.

3. A method of reducing a fractured bone, comprising:
exposing a first portion of a fractured bone having a first intramedullary canal portion;
inserting a rigid distal portion of a reduction device into the first intramedullary canal portion;
inserting a first flexible portion of the reduction device into the first intramedullary canal portion after inserting the rigid distal portion into the first intramedullary canal portion; and
inserting a rigid medial portion of the reduction device into the first intramedullary canal portion after inserting the first flexible portion into the first intramedullary canal portion;
inserting a second flexible portion of the reduction device into the first intramedullary canal portion after inserting the rigid medial portion into the first intramedullary canal portion; and
manipulating the reduction device to reduce the fractured bone including;
flexing the second flexible portion of the reduction device;
rotating the flexed second flexible portion of the reduction device; and
flexing the first flexible portion in response to rotating the flexed second flexible portion.

4. The method of claim 3, wherein manipulating the reduction device to reduce the fractured bone comprises:
positioning a hooked portion of the reduction device in a second intramedullary canal portion of a second portion of the fractured bone.

5. The method of claim 4, further comprising:
inserting a guidewire into a bore within the reduction tool;
inserting the guidewire within the bore into the first intramedullary canal; and
inserting the guidewire within the bore into the second intramedullary canal, such that the guidewire extends between the first portion of the fractured bone and the second portion of the fractured bone.

\* \* \* \* \*